(12) United States Patent
Sanabria Scharf et al.

(10) Patent No.: US 8,932,353 B2
(45) Date of Patent: *Jan. 13, 2015

(54) MAMMARY PROSTHESIS FILLED WITH EXPANDED POLYMER MICROSPHERES

(71) Applicants: Freddy Sanabria Scharf, Bogota (CN); Rodolfo Salmang, Terneuzen (NL)

(72) Inventors: Freddy Sanabria Scharf, Bogota (CN); Rodolfo Salmang, Terneuzen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 13/758,587

(22) Filed: Feb. 4, 2013

(65) Prior Publication Data

US 2013/0150962 A1   Jun. 13, 2013

Related U.S. Application Data

(63) Continuation-in-part of application No. 13/648,928, filed on Oct. 10, 2012.

(30) Foreign Application Priority Data

Nov. 4, 2011   (CO) .................................. 11-150025

(51) Int. Cl.
*A61F 2/12* (2006.01)

(52) U.S. Cl.
CPC ........................................ *A61F 2/12* (2013.01)
USPC .............................................................. 623/8

(58) Field of Classification Search
USPC .......................................................... 623/7–8
See application file for complete search history.

(56) References Cited

U.S. PATENT DOCUMENTS

| | | | | |
|---|---|---|---|---|
| 3,986,213 A | * | 10/1976 | Lynch | 623/8 |
| 5,238,736 A | * | 8/1993 | Tseng et al. | 428/327 |
| 5,246,454 A | * | 9/1993 | Peterson | 623/8 |
| 5,534,023 A | * | 7/1996 | Henley | 623/8 |
| 5,564,439 A | * | 10/1996 | Picha | 604/890.1 |
| 5,961,552 A | * | 10/1999 | Iversen et al. | 623/8 |
| 6,099,565 A | * | 8/2000 | Sakura, Jr. | 623/8 |
| 7,994,229 B2 | * | 8/2011 | Miki et al. | 521/56 |
| 2007/0088434 A1 | * | 4/2007 | Frank | 623/8 |
| 2009/0099656 A1 | * | 4/2009 | Gelda et al. | 623/8 |
| 2011/0029077 A1 | * | 2/2011 | Choi | 623/8 |
| 2011/0106249 A1 | * | 5/2011 | Becker | 623/8 |
| 2011/0264213 A1 | * | 10/2011 | DeMiranda | 623/8 |
| 2012/0010705 A1 | * | 1/2012 | Laghi et al. | 623/7 |

* cited by examiner

*Primary Examiner* — Suzette J Gherbi
(74) *Attorney, Agent, or Firm* — Whiteford, Taylor & Preston, LLP; Joseph L. Morales

(57) ABSTRACT

A mammary prosthesis built from a sack of elastic material or biocompatible material having a sealed interior cavity with the sack having an anterior surface forming a dome and a posterior surface forming a base, with a sealed and seamless interior cavity filled with microspheres of foamed or expanded polymers or a combination of both. The sack may also be permeable to establish equilibrium between body fluids and interstitial volume of the microspheres.

6 Claims, 1 Drawing Sheet

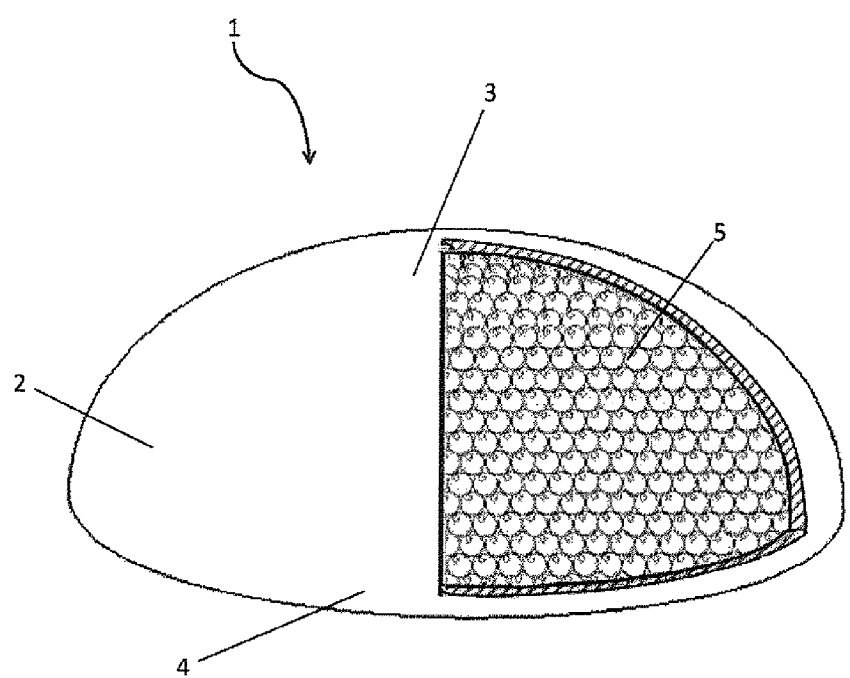

MAMMARY PROSTHESIS FILLED WITH EXPANDED POLYMER MICROSPHERES

This application is a continuation-in-part of application Ser. No. 13,648,928, (the '928 application) filed Oct. 10, 2012. The '928 application is incorporated here by reference.

BACKGROUND

This invention generally relates to a mammary prosthesis, also known as a breast implant, with foamed or expanded and furthermore preferably thermoexpanded polymer microspheres. The inventive implant constitutes an alternative to the existing implants with silicone gel and/or saline solution filling, offering advantages over the existing implants, facilitating removal, mitigating the consequences from ruptures within the mammary pocket (Surgical space formed to place the implant), such as the formation of siliconomas and seromas, a more natural feel to the touch once it is placed, reduced weight and easier removal from the mammary pocket.

Mammary prosthesis or breast implants are indicated in the aesthetic augmentation of breasts and the secondary reconstruction of surgical ablation as an oncological treatment or due to trauma. This surgical indication is found within the reconstructive surgery and cosmetic plastic field. With regard to mammary prosthesis (Breast Implants), developments started over 30 years ago. Research has been done on elastic and resistant wrappings with long term reliability, as well as the use of highly cohesive silicone gel filling, saline solution filling, and soy oil (trilucent).

Due to the technological developments and the broad existing market for this product it is determined to venture in the development of implants for different parts of the body, such as breast, buttocks or testicular implants, among others where the filling is not liquid or a gel, or its combination, and that reduces the complications of the current ones such as deflation and gel migration that can result in seromas, siliconomas, and adenopathies, consequences due to ruptures within the mammary cavity, and a ruptured implant replacement.

As it is mentioned, the existing art in terms of implants presents several disadvantages that are intended to be overcome with the proposed invention, becoming an alternative to what already exists as explained below. In comparison to the generality of the implants, the proposed invention presents advantages in case of rupture avoiding the complications with the existing implants. In the case of saline solution filled implants, it has been observed that once placed, these lose volume over time; and have a less natural feel to the touch, something that is intended to be overcome with the present invention. With regards to silicone gel filled implants, the density of the gel can result in a much heavier implant, and in the event of a rupture, the leak or migration of the gel into the interior of the mammary pocket (Capsule formed by scaring tissue), or even extracapsular leakage can make its removal difficult and produce seromas or siliconomas, which is mitigated by the present invention, by allowing an easier removal of the filling if it ruptures, due to its characteristic shape and defined consistency, not of a fluid. Additionally, because of the easier removal due to the proposed implant characteristics, the resistance improves on account of the expanded polymer microsphere filling; it reduces the weight of the implant and presumably offers a more natural feel to the touch once it is placed.

A breast augmentation using mammary implants must be done in a surgical environment (operating room), by surgeons specialized in plastic surgery. Among the surgical techniques, to do this type of procedure, the surgeon must use entry routes depending on the area of the scar. The most used entry route is the areola (around the nipple). A second modality is the axillary route (in the armpit) and a third commonly used route is the sub-mammary, which is done in the inferior fold of the breasts.

As such, the implant must be placed in one of the two available places in the human body, the prepectoral located between the mammary gland and the retro-pectoral, behind the mayor pectoral muscle. It is the surgeon's responsibility to assess the size and shape of the implant, where the incision will be made in the breasts, the approach, and the criteria for positioning the implant as a function of the patient's anatomy and the expected aesthetic results.

Some combined systems have been developed, which include gel with silicone microspheres. This development is found in the U.S. Pat. No. 4,380,569 issued to Shaw on Apr. 19 1983, where a mammary prosthesis is described with a reduced weight and made of a mixture of a gel and silicone microspheres dispersed within the fluid. In this proposal the weight is reduced, but the problem of liquid pressure, friction, and the use of gel persists, with the disadvantages already mentioned.

SUMMARY OF THE INVENTION

Being as it is, it is an object of the present inventive implant to be an alternative solution to the generality of the silicone gel, saline solution, or combination of both, filled implants, constituting in a novel implant where the filling is comprised of microspheres made of a biocompatible and expandable material, within a silicone sack or any other biocompatible material that serves as a receptor or net for the microspheres. The purpose being that the present inventive implant will solve or mitigate the problems that presently available implants currently have. For purposes of this invention, the prefix micro as used in the term microspheres can be interpreted as belonging to the range between 0.001 mm and 0.5 mm and from now on it is normally referred as tenths of a mm. This range should not exclude a larger value like 1.0 and even 2.0 mm.

The present invention is generally related with a mammary prosthesis (Breast Implant) with expanded polymer spheres filling. Preferably microspheres, and preferably thermoexpanded (heat induced expansion), within an expansion range ideal for the application., where the degree of expansion can be defined by the density or preferably the specific gravity referenced to the density of water, within a range that goes from 1.0 [not expanded], to 0.03 [maximum practical expansion]). The range of expansion mainly defines the resilience properties as well as the apparent density. In an alternate embodiment other reduced size corpuscles could be used—not necessarily round—and of different materials. Particularly, the invention consists of a mammary prosthesis built from a sack (Bag) or shell with an interior cavity, made of an elastic material, that has an anterior side that forms a dome and a posterior side that forms the base, the sack having a configuration that resembles the female breast that is full and sealed, that includes an expanded polymer microspheres filling; where the microspheres could be contained in a silicone sack (wrapping) or an appropriate biocompatible elastomer, or in a net like sack of a biocompatible material where the elastic material has enough resilience to maintain the shape of the implant that was originally defined. The materials used in this implant are FDA approved materials for direct body contact use. The inventive implant invention is presented as an alternative to the existing implants with silicone gel, saline solution, or combined filling, offering advantages over the existing art: avoiding volume loss, reduced weight alternative; providing easier removal from the mammary pocket if ruptured, and mitigation of the consequences from ruptures within the mammary pocket, such as the formation of siliconomas and seromas. As another alternative it can improve the resistance, and offers a more natural feel to the touch once it is placed.

Therefore, it is a distinct object of the present invention to avoid the disadvantages and complications of the previous art, and become an alternative. More particularly, the object of the proposed invention is to improve the previous art, where the mammary implant is made of a sack (bag) or receptor that looks like the mammary sack, made of silicone or any other biocompatible material that ideally maintains its originally defined shape, that will have biocompatible polymer microspheres as its only and exclusive filling, where the implant as a whole, sack and filling, result in an implant that avoids or mitigates the complications of the previous art. This is particularly so because it results in an implant that mitigates the loss of volume like the saline solution ones, and the consequences of a ruptured silicone gel implant inside the mammary cavity or "bleeding" (permeation of the gel trough the elastomer membrane into the scaring capsule), allowing a much easier removal of the filling compared to what happens with a material like silicone gel. Additionally, the stability of the material compared to the liquids and gels allows it to be easily removed from the mammary pocket compared to the existing arts, to be lighter than the previous art, and possibly have greater resistance and durability. The present invention fulfills these needs and offers other related advantages.

The novel characteristics that are considered as the basis for the invention are particularly explained in the attached claims and the additional advantages of the implant, will be better understood in the following detailed description with the preferred modalities and the appropriate reference to the pictures that go with it.

BRIEF DESCRIPTION OF THE FIGURES

To make the invention and its advantages more clear compared to the known art, the possible illustrative and nonlimited form of embodiment of the application of such principles, are described below with the help of annexed pictures.

FIG. 1 shows an isometric view of the inventive mammary prosthesis with a partial cut away of the surface of the inventive prosthesis in its preferred modality.

DETAILED DESCRIPTION OF THE INVENTION

Particularly, based on FIG. 1, the invention consists of a mammary prosthesis 1 built from a sack 2 or shell with an interior cavity, made from an elastic material such as a silicone elastomer, or any other biocompatible material that serves as a sack, net or mesh, or receptor for the microspheres 5. Conveniently, the shell material can include a bag made of silicone elastomer, or from a new line of development for skin substitutes and tissues that can give a better support to the implants in mammary reconstructions or nets for defects or hernias, that can eventually replace the implant shell. The most common ones are acellular dermis, which is a skin layer without cells that may produce an immunological response from the organism, Flex HD® from Johnson & Johnson, Dermamatrix from Synthes, Alloderm® from lifecell, or a biocompatible net like sack.
In the case of a net sack, the spacing between the filaments is smaller than the spheres diameter to insure the containment of said spheres, and furthermore, small enough to avoid scar tissue growth through said spaces. The net sack does not need to be impermeable to liquids, as the sterilized air or gas volume residing within the spheres interstices may be replaced by the body liquids finally reaching an equilibrium state and still maintain the desired characteristics of resistance to deformation.

The prosthesis 1 consists of a sack 2 formed from an anterior surface that makes a dome 3 and a posterior surface that forms the base 4, where the sack 2 resembles the female breast.

Such sack 2 is fully filled with a plurality of microspheres 5. The microspheres 5 may be contained in a silicone sack or in a net like sack made from a biocompatible material. Such microspheres are made from foamed or thermo-expanded polymers such as ePTFE polytetrafluoroethylene or polystyrene or a combination of several materials approved for permanent and direct contact with the human body. The C.O.F (coefficient of friction) of the spheres together with their packing bulk density, determine in a great extent the resulting resistance to deformation of the prosthesis, and hence impart a characteristic feeling that is similar to the natural feeling. The apparent C.O.F can be thus adjusted within a range of 0.03 to 0.70

Optionally, such microspheres can have a nucleus made from a material, covered with a different material, as long as these materials have a selection of biocompatible material.

As such, the sack is sealed, so that the microspheres do not come in contact with the mammary cavity. The sealing system can be the same one that is used with the current implants, although it doesn't preclude other alternatives, and the sack may be seamless.

As such, the implant of the present invention must comprehend several sizes to balance out the differences in breast shapes, offering the surgeon a wider range of options; these configurations are available in a smooth or textured surface and would be available in several shapes including but not limited to round and tear drop (also called anatomical).

Due to the manufacturing requirements of the sack or net, the right material for it is silicone, but it could also be any other biocompatible material that serves as a sack or receptor for the microspheres. It can be a material manufactured and marketed by NUSIL Technology® (certified ISO 9001).

Only some preferred modalities of the invention have been illustrated as examples. In this respect, it is observed that in the construction of the mammary implant, as well as the details in its configuration, there are many alternatives to choose from without deviating from the spirit of the invention according to the following claims.

We claim:

1. An implant, comprising:
   a) an implantable sack having a sealed interior cavity;
   b) wherein the sealed interior consists of microspheres made from biocompatible particulate material comprised of a foamed or thermo-expanded polymers; and
   c) wherein the biocompatible material has enough resilience to maintain the shape of the implant and the implant is a mammary implant.

2. The implant claim 1, where the microspheres have an expansion range between a specific gravity of 1.0 to 0.03.

3. An implant according to the claim 1, where the microspheres have a coefficient of friction ranging from 0.03 to 0.70.

4. An implant according to the claim 1 where the sack is made from a mesh, net, or skin substitute.

5. An implant according to claim 1, where the biocompatible particulate material is made of ePTFE.

6. An implant according to claim 1, where the sack or shell of the implant is made of a silicone elastomer.

* * * * *